United States Patent
Johnstone et al.

(10) Patent No.: US 10,076,675 B2
(45) Date of Patent: Sep. 18, 2018

(54) BEAM DELIVERY SYSTEM FOR PROTON THERAPY FOR LASER-ACCELERATED PROTONS

(71) Applicant: HIL Applied Medical Ltd., Jerusalem (IL)

(72) Inventors: Carol Johnstone, Warrenville, IL (US); Shmulik Eisenmann, Pardes Hana-Karkur (IL); Sagi Brink-Danan, Jerusalem (IL)

(73) Assignee: HIL Applied Medical Ltd., Jerusalem (IL)

( * ) Notice: Subject to any disclaimer, the term of this patent is extended or adjusted under 35 U.S.C. 154(b) by 0 days.

(21) Appl. No.: 15/275,876

(22) Filed: Sep. 26, 2016

(65) Prior Publication Data

US 2017/0087390 A1    Mar. 30, 2017

Related U.S. Application Data

(60) Provisional application No. 62/234,732, filed on Sep. 30, 2015.

(51) Int. Cl.
*A61N 5/10* (2006.01)

(52) U.S. Cl.
CPC ......... *A61N 5/1081* (2013.01); *A61N 5/1043* (2013.01); *A61N 2005/1087* (2013.01); *A61N 2005/1088* (2013.01)

(58) Field of Classification Search
CPC . A61N 2005/1087; A61N 5/10; A61N 5/1077
See application file for complete search history.

(56) References Cited

U.S. PATENT DOCUMENTS

| | | | |
|---|---|---|---|
| 8,389,954 B2 | 3/2013 | Zigler et al. | |
| 2009/0050819 A1* | 2/2009 | Ma | A61N 5/10 250/396 ML |
| 2011/0121194 A1* | 5/2011 | Bhatt | H01J 23/02 250/396 ML |
| 2014/0094641 A1* | 4/2014 | Gall | A61N 5/1077 600/1 |
| 2014/0243576 A1* | 8/2014 | Kakutani | A61N 5/1077 600/1 |
| 2015/0038764 A1* | 2/2015 | Sugahara | A61N 5/1079 600/1 |

* cited by examiner

*Primary Examiner* — Christine H Matthews
(74) *Attorney, Agent, or Firm* — Manelli Selter PLLC; Edward J. Stemberger

(57) ABSTRACT

Laser accelerated Proton beams provides compact sources for Proton beams. This invention describes several examples of optic designs which provide a compact beam delivery system capable of supporting pencil beam scanning and delivering the required clinical dosage in a tight beam spot.

8 Claims, 9 Drawing Sheets

BEAM DELIVERY SYSTEM FOR PROTON THERAPY FOR LASER-ACCELERATED PROTONS

TECHNOLOGY FIELD

The system relates to the field of proton beams generation and in particular to a system for focusing and controlling the delivery of laser accelerated protons a method thereof.

BACKGROUND

Proton Therapy was developed after WWII and has become a standardized radiological treatment applied to different anomalies and especially for treatment of tumors in different locations in the human body. Proton therapy utilizes a beam of charged and accelerated particles—protons. Such proton beam could be delivered to tumors with significantly less dose to normal tissues and organs than conventional radiotherapy.

Proton beams work on the principle of selective cell destruction by exploiting the Bragg energy peak of ion beams which localizes the majority of the energy distribution of an ion beam within a small physical range. The major advantage of proton treatment therefore over conventional radiation treatments is that most of the energy of the proton beam can be directed and deposited in tissue volumes designated by the physicians-in a three-dimensional pattern by locating the Bragg peak within that volume and changing the beam accordingly during treatment. This capability provides greater control and precision and, therefore, superior conformal dose distribution to conventional photon radiotherapy including Intensity Modulated RadioTherapy (IMRT). Radiation therapy with photons requires that conventional x-rays be delivered into the body in doses sufficient to assure that enough ionization events occur to destroy tumor cells but entrance and exit doses to normal tissue are generally higher than the individual dose to the tumor in a given field.

Advances in ultra-compact laser-driven proton acceleration systems as described in U.S. Pat. No. 8,389,954 provide a means for practical use of proton beams. In order to provide a therapeutically viable proton beam, the low energy protons and broad energy spectrum characteristic of the primary beam must be separated and the remaining proton beam tailored in terms of proton energy spread to meet well-defined clinical criteria. In addition the proton beam must be focused to a small spot size suitable for Pencil Beam Scanning (PBS). The beam delivery system is responsible for separating, tailoring and focusing the proton beam. Existing and standard approaches to beam delivery systems fail to address the large spread in proton energies and angular distribution as typical in laser driven acceleration systems. Furthermore, despite their limited performance existing beam delivery systems are too large to be used with the compact laser driven acceleration systems that could reduce the system foot print and save expensive clinical space.

DESCRIPTION

Therefore in general, the industry would welcome a compact beam delivery system for proton beams from ultra-compact laser-driven proton acceleration systems.

An example of desired criteria for clinical systems proton beams are given in the table below:

| Parameters | Nominal | Minimum | Maximum |
| --- | --- | --- | --- |
| Range | N/A | 2 cm (70 MeV) | 22 cm (250 MeV) |
| Field Size | 10 × 10 cm | 10 × 10 cm | 30 × 30 cm |
| Spot Size (FWHM) | 5 mm | 3 mm | 10 mm |
| Energy Modulation Rate | 0.1 sec | N/A | N/A |
| Energy Bite (FWHM) | ±1% ΔE/E | ±0.5% ΔE/E | ±1.5% ΔE/E |
| Targeting Accuracy | 0.5 mm | 0.2 mm | 1 mm |

An example of size requirements of the beam delivery system are less than; 2.5 m in height; 4.5 m in length; 0.9 m to 1.1 m and typically 1.0 m; Source Axis Distance (SAD) between the exit of the last scanning magnet and the patient.

One of the technical difficulties lies in pencil beam scanning which generates substantial and varying dispersion of off-momentum particles at isocenter depending on the offset required to treat the gross tumor volume. Canceling even the lowest order dispersion term created by scanning magnets requires large aperture quadrupoles sandwiched between the pair of scanning magnets which would then require a much larger SAD (Source Axis Distance) distance of at least an additional meter or more. At best, conventional nonlinear correctors, sextupoles in the case of chromatic correction, only allow ~±2% Δp/p to be delivered within the position targeting specifications to isocenter. Even capturing the laser-driven proton beam with a strong super conducting (SC) solenoid exhibits strongly achromatic properties in the off-momentum optics.

Therefore in general, compactness is nominally incompatible with delivering a large momentum spread without aberrations using conventional linear Proton beam optics. In proton beam delivery design, the beam source is defined in terms of a standard set of beam parameters. The function of the beam delivery system is to manipulate the beam parameters to attain the target beam parameters. Each component of the beam delivery system performs a defined manipulation and the action of the beam delivery system is obtained by sequential application of all the manipulations. The source beam parameters are derived from the beam's phase space distribution immediately after the proton beam accelerator. The parameters relate to the distributions of the position and angles of individual protons as expressed in a curvilinear coordinate system termed phase space. Linear dynamics allow derivations of beam parameters through magnetic fields. The beam's phase space is described by an elliptical function;

$$\gamma x^2 + 2\alpha x x' + \beta x'^2 = \epsilon$$

Figure 1:
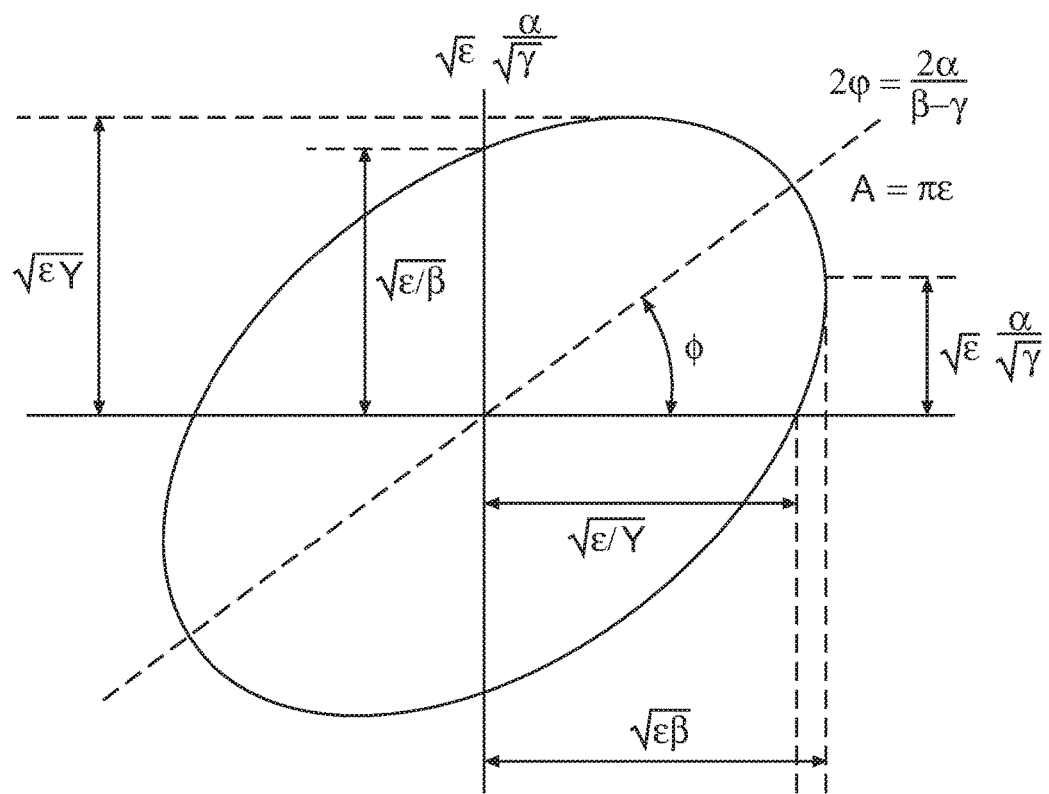
FIG. 1 is an example of a phase space distribution of particles on ellipsoids from an accelerator with predominately linear dynamics.

The emittance c, is defined as the area of one of the (concentric) ellipsoids and $\beta$ and $\alpha$ represent the equation of the ellipse ($\gamma = \sqrt{(1+\alpha^2)/\beta}$) (x and x' are location and it's derivative, i.e. velocity). FIG. 1 is an example of a phase space distribution of particles on one of the ellipsoids from an accelerator with predominately linear dynamics. The emittance is the area of the ellipse $=xx'/\sqrt{(1+\alpha^2)}$.

Figure 2:
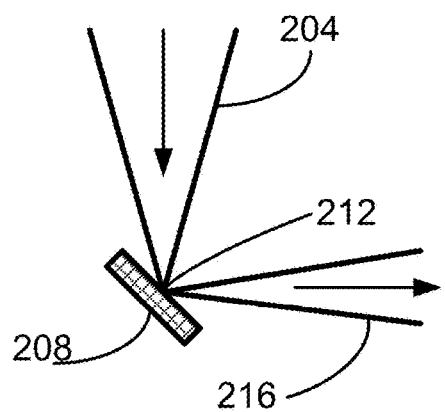
FIG. 2 is an example of a layout of a laser generated proton spot source.

FIG. 2 is an example of a layout of a laser generated proton spot source. Laser beam 204 is directed towards target 208 such as the target disclosed in U.S. Pat. No. 8,389,954 to same assignee and incorporated here by reference and is focused on it onto a spot 212 of about 100 micron size causing emission of a beam of proton particles 216. The proton beam has a relatively large divergence $\Omega$ of about or less than 0.1 steradian.

Laser accelerated proton beams have different characteristics than beams produced in a conventional particle accelerator with radiofrequency electric-field cavities accelerating structures and magnetic confinement. Linear and circular accelerators nominally produce a typical elliptical phase space distribution with a 3σ emittance typically in the range 7-20 π mm-mr and with a total momentum spread less than a 1%. Beam sizes are characteristically centimeters and divergences are significantly less than 1°. The beam example of FIG. 2, in contrast to conventional beams, has an extremely small spot size extremely large divergence and momentum spread. These characteristics have been addressed in the present beam delivery system.

One example of laser accelerated proton beam parameters are

Proton energy: 250 MeV
Source size: 10-100 m
2D Divergence angle: ~0.2 rad (~11 degrees)
Energy angular distribution:

$$\frac{\partial \Omega}{\partial E} = 0$$

Proton number energy distribution:

$$\frac{\partial N}{\partial E} = 0$$

Number of protons per laser pulse: $10^8$
Repetition rate: 10-1000 Hz

For these specifications, the laser-generated emittance is at least factor of 2-3 smaller than a conventional linac, cyclotron, and other known technologies.

$$\epsilon = 50 \times 10^{-3} \text{ mm} \times 52.36 \text{ mr} = 2.62 \text{ mm-mr}$$

The betatron functions at the focal point are derived by;

$$x = \sqrt{\beta \epsilon}; \beta_{x \text{ or } y} = \frac{x^2}{\epsilon} = \frac{(0.05)^2}{2.62} = 0.001 \text{ m}$$

The small spot size 212 formed by laser beam 204 and large divergence of proton beam 216 require a novel beam capture solution. Laser beam generated proton beam has a rotational symmetry. In one example, a solenoid whose end field focuses equally in all directions is used the first optic for beam capture. Although the solenoid couples the two planes and angular momentum rotates any initially-defined orthogonal planes; the rotational symmetry of the laser accelerated beam negates any consequences of this rotation. The solenoid is used to exchange angle for position; i.e., a larger beam for a smaller divergence which is more easily managed by conventional beam confinement components. Although the beam is "coupled" by the solenoid and the transformation of its parameters is calculated with coupled planes, due to the axial symmetry of the beam, once outside the solenoid field, the rotation can be ignored and the x-y planes re-established for the rest of the beam delivery system optics.

In a further example, the solenoid is a superconducting high magnetic field solenoid of 9-15 T. In additional examples the solenoid magnetic field is 10 T and in another example the solenoid magnetic field is 15 T. In one example the solenoid length is 0.6 -0.85 m. In another example the solenoid length is 0.55 m.

In another example integrated strength of the magnetic field was 7.8 T-m and the focal length was 1.9 m. In a further example the laser accelerated beam source and solenoid are separated and spaced apart from the patient treatment area.

In an additional example a solenoid with a magnetic field of 15 T with a beam size diameter of 3.5 cm and a solenoid aperture diameter of 4 cm was used. In a further example the solenoid diameter is larger than 4 cm. In another example of a solenoid with a field of 10 T the aperture increases by 40%.

Figure 3:
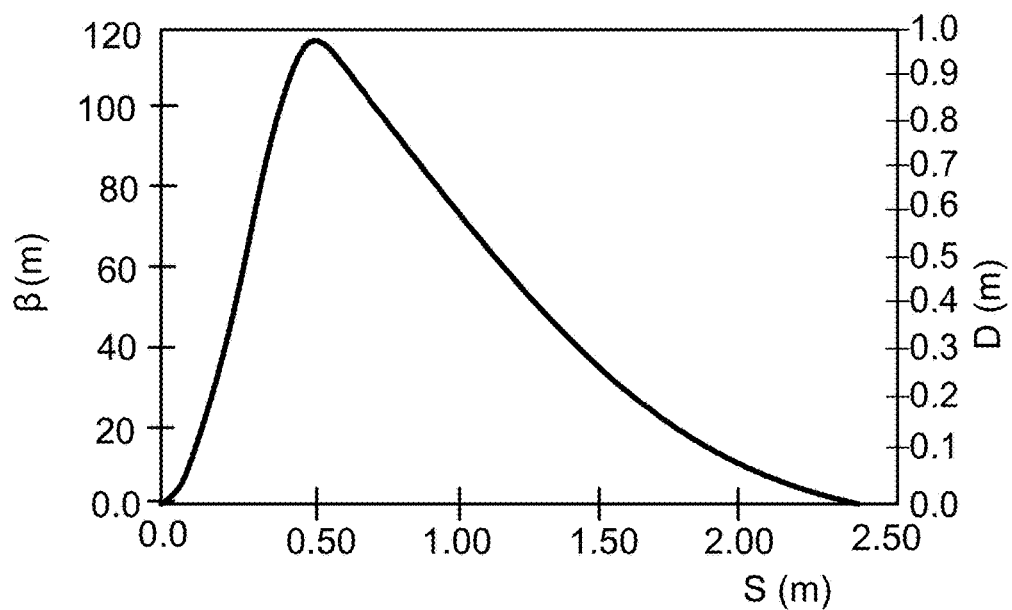
FIG. 3 is an example of the propagation of proton beam through a solenoid.

FIG. 3. is an example of the propagation of proton beam through the solenoid and downstream drift to waist ($\beta$=0.025 m) and off-momentum performance for a $\Delta p/p$ of ±10%. The magnetic field in the example of FIG. 3 is 15 T.

In this example the proton beam focus after the solenoid is a factor of 25-30 larger in beta functions than the waist at the exit of the accelerator. In this example the divergence has been decreased by the square root of this factor. In one example the distance between the laser source point and the solenoid is 5 cm. In a further example the distance is larger than 5 cm and smaller than 15 cm. In a further example, the distance is 10 cm and the solenoid aperture is larger than 5 cm.

Figure 4:
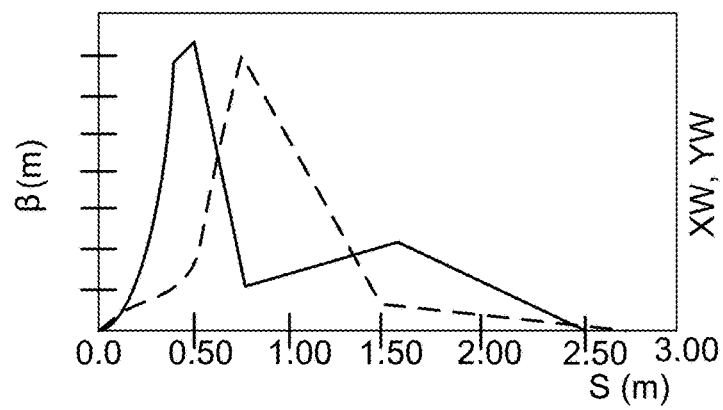
FIG. 4 is an example of the propagation of a beam through a quadrupole capture.

In another example the capture optics is realized with a quadrupole. In one example the distance between the laser beam 204 accelerated proton beam source or target 208 and the quadrupole magnet is at least 10 cm, proton beam size is 6, 7 cm or any value between 6 and 7 cm and a quadrupole magnet aperture of 8 cm. The distance between the capture quadrupoles and upstream quadrupoles is 0.6 m. In a further example a combined function quadrupole which provides both capture as well as upstream optics can be used. In a further example a quadrupole can provide chromatic aberration correction to increase the useful momentum spreads at isocenter. FIG. 4 is an example of the propagation of a beam through a quadrupole capture and matching and off-momentum performance for a dp/p of ±5%. Gantry rotation could begin immediately downsteam of this section.

Figure 5:
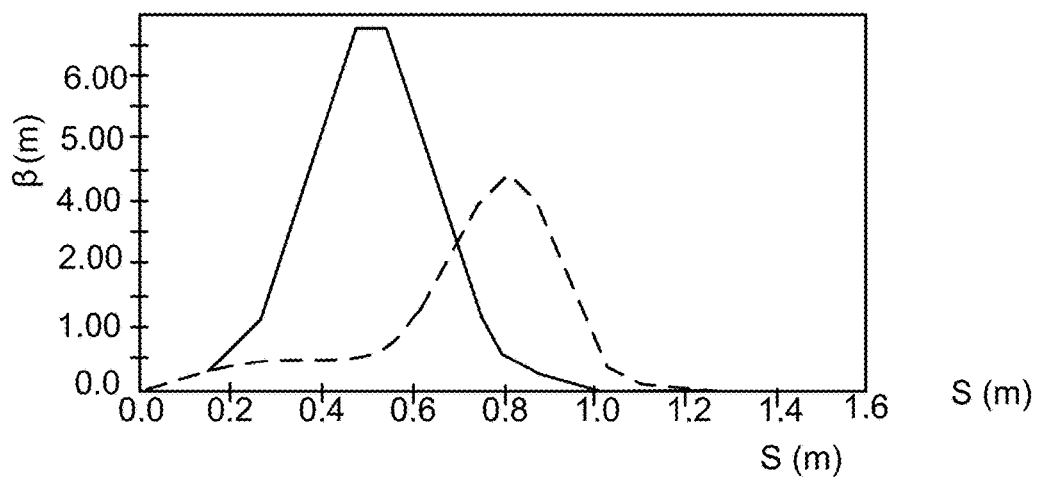
FIG. 5 is an example of the propagation of beam through a quadrupole capture channel with reduced poletip fields to normal conducting range.

In one example the second quadrupole is 3.5 times longer than the first quadrupole to reduce the poletip field to normal conducting status. The optics do not change in contour nor the quadrupole layout, but peak beta functions rise considerably to 500 m after the double peak is optimized. FIG. 5 is an example of the propagation of beam through a quadrupole capture channel with reduced poletip fields to normal conducting range. Peak beta functions are projected to be around 500 m. In a further example a fifth quadrupole provides the match to rotationally invariant optics to prepare for the gantry. Thus the final aperture of the two peak-beta quadrupoles will be at least 8 cm or 9 cm. In a further example a dipole component can be introduced in the quadrupole gradient, which is a combined function magnet. The dipole component will separate the far off-momentum particles prior to the beam entering the gantry and minimizing the required shielding around the primary momentum collimator.

In a further example the normal-conducting quadrupoles are operated with a DC current. In still a further example the normal-conducting quadrupoles are operated with a pulsed current to reduce power consumption. In an additional example the normal-conducting quadrupoles are operated with a ramped current to enhance the energy change rate.

In one example the parameters of the quadrupole capture channel referenced to normal conducting strengths evaluated at 250 MeV are as shown in the table below.

| Magnet code name | Type | Rep rate | Length (cm) | Aperture diameter (cm) | Gradient (T/m) | Poletip field (T) |
| --- | --- | --- | --- | --- | --- | --- |
| Q1Q | NC | DC | 9 | 2.0 | 134 | 1.3 |
| Q2Q | NC | DC | 33 | 8.0 | 38 | 1.5 |
| Q3Q | NC | DC | 24 | 8.0 | 38 | 1.5 |
| Q4Q | NC | DC | 14 | 4.0 | 57 | 1.1 |
| Q5Q | NC | DC | 7 | 1.5 | 112 | 0.8 |

A two collimator gantry was tested. The two collimators are able to generate a smaller than a single collimator ΔE/E. A single collimator gantry requires a smaller number of parts and has a smaller footprint. The single collimator gantry also produces less secondary emission in the collimator. Both configurations seem to be suitable for the task of generation of laser accelerated proton beams system and in particular to a system for focusing and controlling the delivery of laser accelerated protons a method thereof. The following description concentrates on a single collimator laser accelerated proton beams system since it supports a smaller footprint or a reduced area layout.

Figure 6:
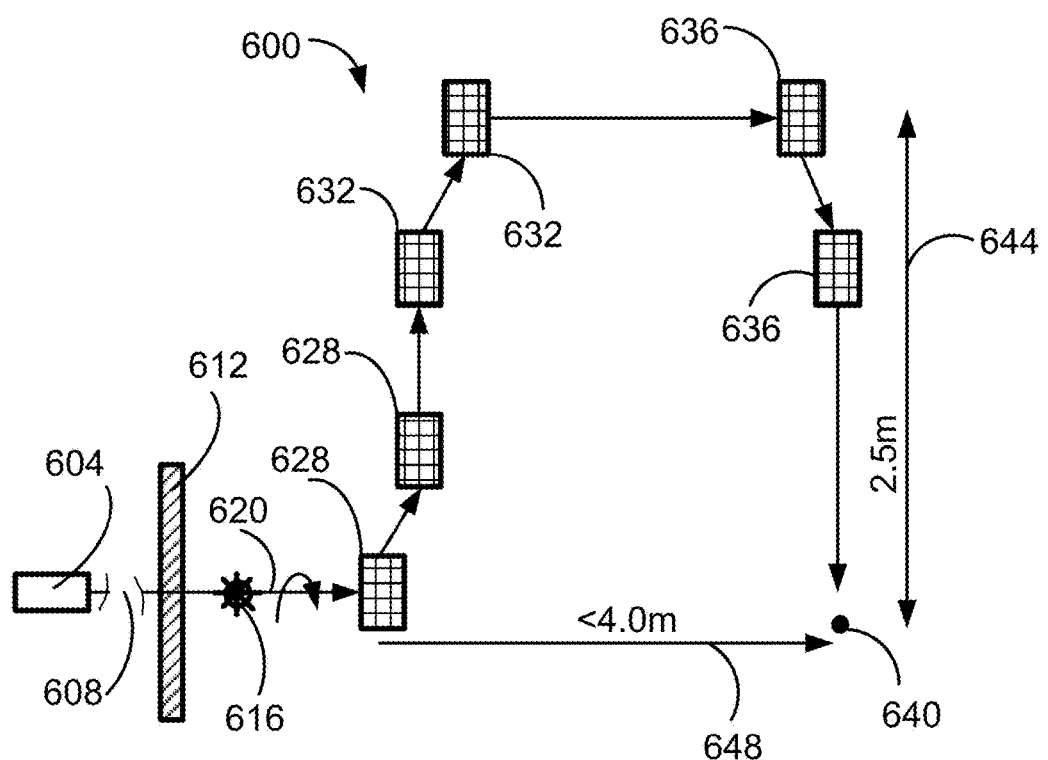
FIG. 6 is an example of the optics of a single collimator gantry layout.

FIG. 6 is an example of the optics of a single collimator gantry layout. In the figure reference numeral 604 marks solenoid located at a distance 608 of about 0.9 m to 1.1 and typically at 1.0 meter from single collimator gantry 600 marked by a wall 612. Numeral 620 marks axis of rotation of coupled planes about the axis of solenoid 604 and 640 is isocenter of the gantry.

In one example gantry 600 dipole layout uses a magnetic field of 4.8 T, 0.6 m long dipole pairs 628-636 with each pair bending 45° to form the rectangle. The two long straight sections 644 and 648 can be adjusted independently providing significant tuning range, flexibility and therefore customization in the optics which is needed to achieve a corresponding large range in clinical beam specifications. In one example the 90° bends are split into two for better reference trajectory control. Each of dipole pairs 628-636 can be adjusted independently, and economically through shunts on a single power supply with at least 10% variation and a total of 20% total relative change between them. These dipole pairs allow for independent trajectory correction on each arm of the gantry and to isocenter thus decreasing the tolerances and cost associated with a precision gantry. In the example of single collimator gantry 600, the gantry has a reduced area layout of about 2.5×4.0 sqm.

The system for delivering charged particles to treat a patient, includes an ion source 208 (FIG. 2) configured to provide an ion beam 620 substantially symmetric in phase space; a conduit for providing a path for the ion beam; at least one electromagnet 628-636 associated with the conduit or proton beam pass 620, the at least one electromagnet being configured to direct the ion beam 620; a rotatable gantry 600 for supporting the at least one electromagnet 628-636 for rotating the at least one electromagnet 628-636 about a patient treatment zone.

In another example the dipoles can be replaced by equivalent-strength super ferric SC dipoles. In one example the peak magnetic field of the SC dipole is 5 T. In another example the DC dipoles have a peak magnetic field of 1.4 T.

In a further example the momentum collimator for the energy selection system (ESS) could be positioned on the longer horizontal arm to take advantage of the length relative to the first or shorter arm of the gantry. The length of the momentum collimator is designed to meet the specified ±2% Δp/p control over momentum spread at isocenter 640. In a further example the beam has a 2 cm beam size, full width, and the momentum collimator has a length of 1 m.

In further example the full beam width (95-99%) of the beam at isocenter is either 1 cm or 0.6 cm or any value between 1 cm and 0.6 cm.

To achieve PBS (Pencil Beam Scanning) the separation between beam steps could be about half the full width of single collimator gantry. A Gaussian or smooth falloff tail is acceptable for PBS as individual beam spots must overlap for smooth proton dose distribution. Therefore the effective beam spot is 3 mm to half a centimeter for example, were used in the tests. In a further example the beam is circular with the same divergence in all directions so that the rotation of the gantry does not impact the optics at isocenter; i.e. the beam displays rotational symmetry on entering the rotating section and gantry proper.

The examples described above provide a factor of 5 or more reduction of the 2% specification in Δp/p and provide a momentum bite control of <0.4% Δp/p.

Figure 7:
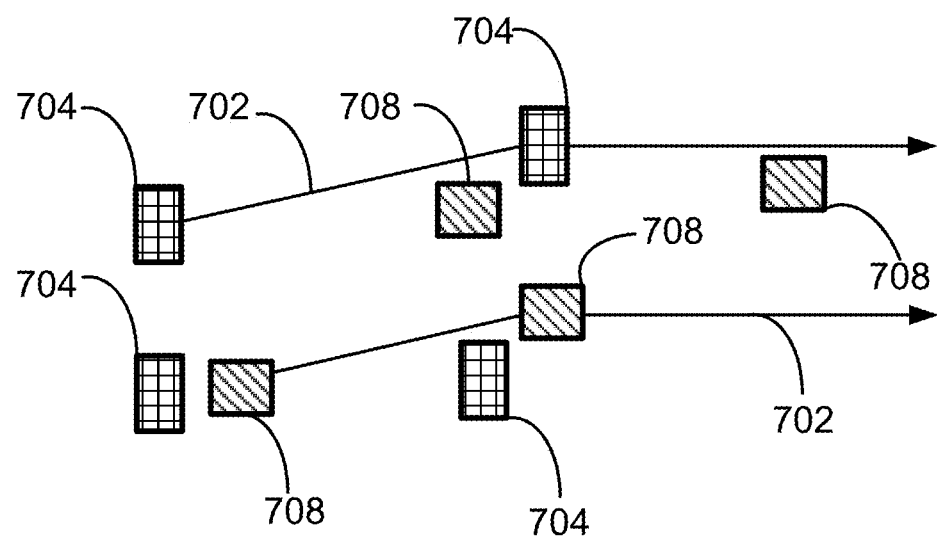
FIG. 7 provides examples of the aperture issues associated with dual plane magnetic scanning.
Figure 8:
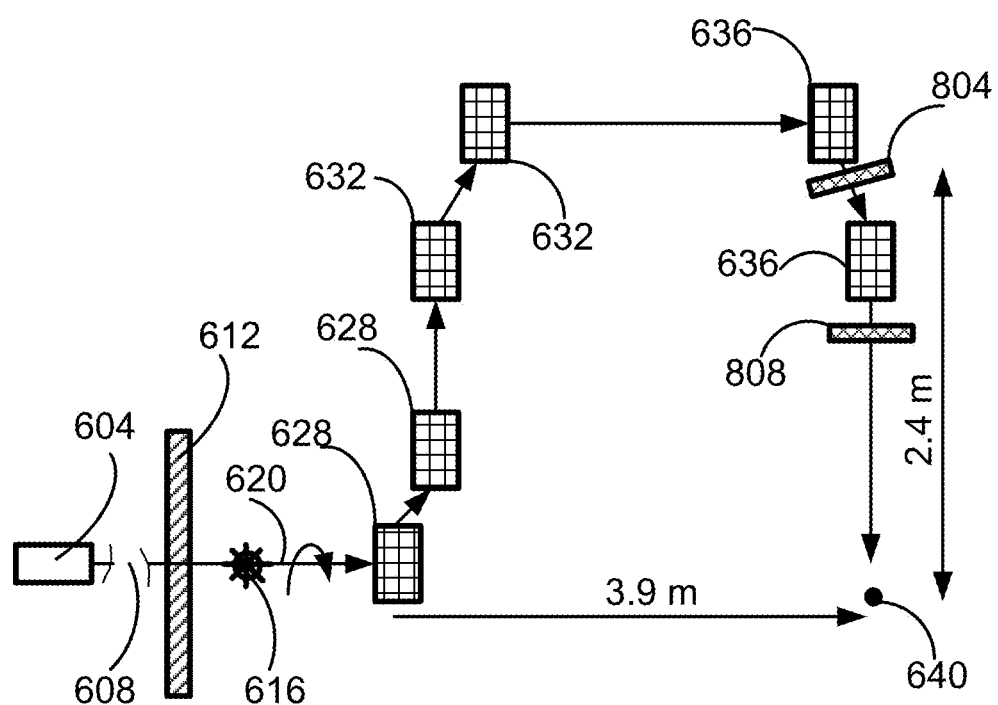
FIG. 8 is an example of two scanning magnet configuration.

Implementing both vertical and horizontal PBS scanning is technically challenging. FIG. 7 provides two examples of the aperture issues associated with dual plane magnetic scanning where numerals 704 represent a scanning magnet, which moves the proton beam 702 in the plane of the gantry and numerals 708 a scanning magnet which moves the proton beam 702 out of the plane of the gantry. FIG. 8 is a further example of two scanning magnet configuration; in-plane view of gantry (top) and out-of-plane view (bottom) for scanning in plane of single collimator gantry and out of plane magnets 804 and 808 In order for proton beam to clear for a 20×20 cm field or larger, the gap was increased (>20 cm) in at least two of the magnets 804 and 808. Other parameters of the tested layout were SAD about 1.4 meter, distance between the scan magnets 804-808 was 0.77 meter; travel required at the second (708?) magnet was +/−0.125 meter; downstream gap for the second 45 degrees magnet 532 was 0.1 meter at 20 cm gap.

One example of a solution to the beam scanning challenge is scanning in one plane only and moving the couch (not shown) on which the patient is positioned in the opposite plane. In this example two degrees of scan are achieved without large aperture scanning magnets.

In another example the couch moves along the plane of the single collimator gantry and the two out-of-plane scanning magnets then scan orthogonal to the bend plane of the gantry. This reduces the technical complexity, expense, and potential for failure in magnetic guidance and components. This example further provides a compact 2.5 m single collimator gantry height. Since the power of a dipole goes as the volume and a dipole with a large gap is not only expensive and requires enormous stored power, but field quality and fringe field effects are very difficult to control; the extent of the fringe field is approximately two gaps. For a 20×20 cm field, the gap of the final scanning magnet would need to be 20 cm, which is a challenging target. In contrast a large aperture in the bend plane is relatively easy to implement in a dipole design. Rails for the couch movement are more economic to implement than a precision gantry. Further, couch rails and related motion technology are ultra-stable and precise and much easier to align and verify to less than 25 micron precision. Hence in one example the couch is located on a system of rails and moved by electronic motors or motion controllers to an accuracy better than 25 micron. In a further example the beam is scanned in the out of plane.

Figure 9:
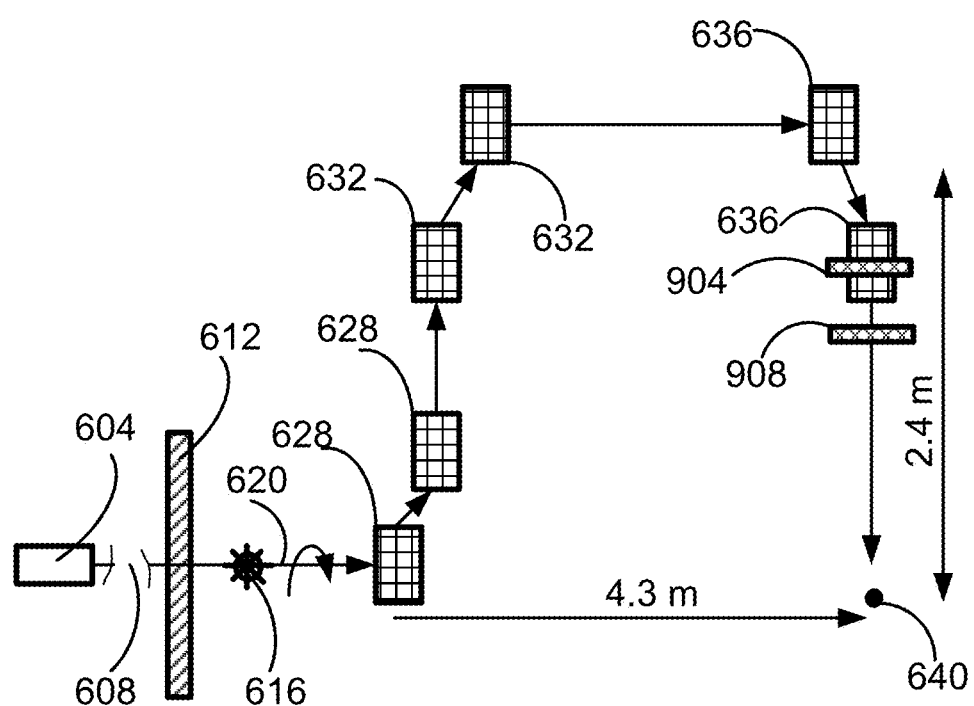
FIG. 9 is an example of a scanning layout with out of plane magnets only.

FIG. 8 which is also an example of a scanning layout with a first scanning magnet between primary bend dipoles. FIG. 9 is an example of a scanning layout with out of plane magnets.

The example of FIG. 8 does not provide a satisfactory solution. The focusing end effects from the rectangular edge effectively canceled the kick from the out of plane scanning magnet. To compensate an in-plane focusing quadrupole was then added. In a further example an out of plane focusing quad is implemented downstream of the bend dipoles to further straighten the kick and maintain correct spot properties at isocenter. In a further example an outward edge angle, as in a sector bend, was introduced in the second dipole of the final pair to change the sign of the kick and enhance the effect of the first scanning magnet. Once again a satisfactory solution to the optics was difficult to achieve—even when a variety of combinations were explored to maintain symmetry in the dipoles throughout the single collimator gantry. It became clear that given the strong horizontally focusing body field of these dipoles, a horizontally defocusing end field effect was important to the stability and tunability of the single collimator gantry optics. (The directional terminology used in the present disclosure is related to the drawings only and does not limit other spatial positions of the gantry.) Another consideration was that "kicking" through the last primary bend dipole increased its gap significantly – to ~6-10 cm depending on the distance to the second scanning magnet. However, the increase in gap is problematic.

FIG. 9 is also an alternative example which avoids the large offset at the exit of the scanning magnets 904 and 908 and also mitigates the focusing effect of the exit end fields significantly. The coils used in the example of FIG. 8 are commonly used in MRI machines.

Figure 10:
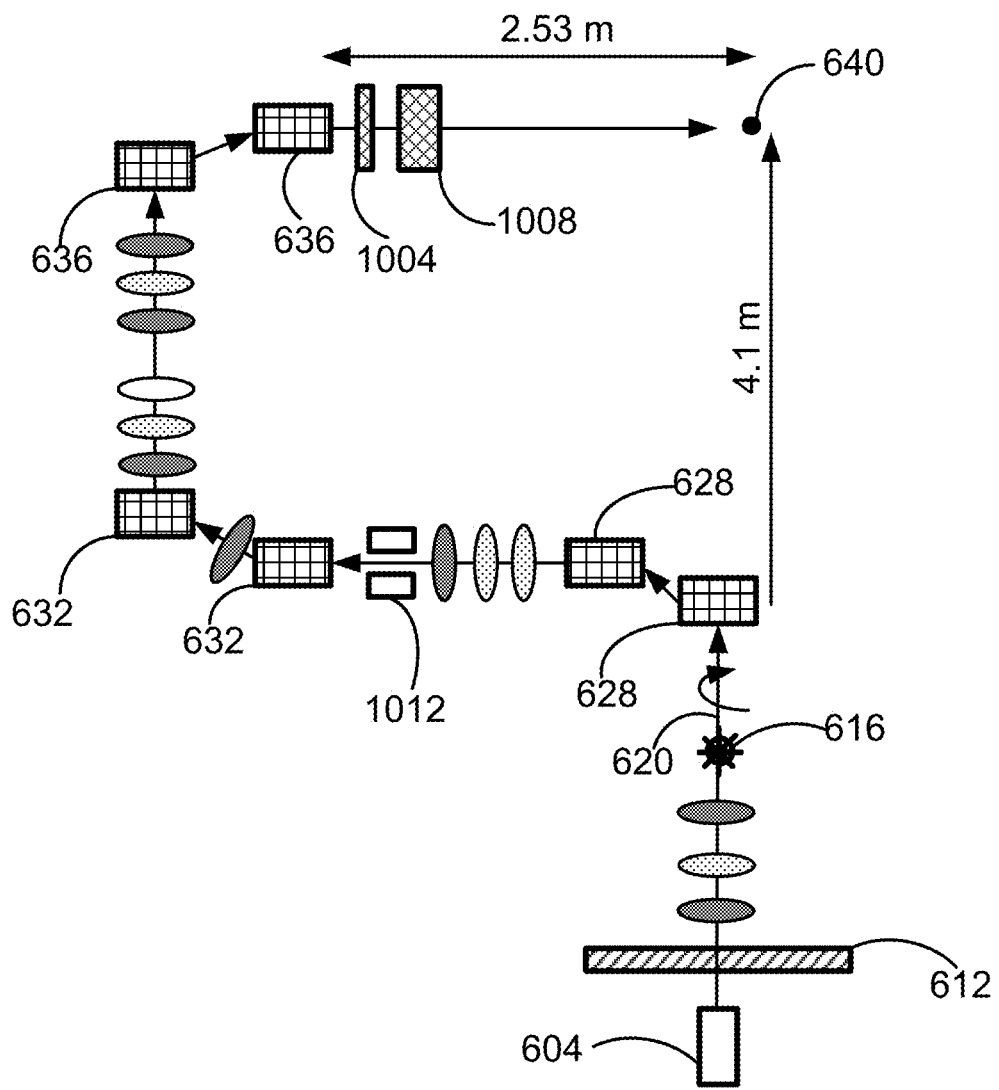
FIG. 10 is an example of a scanning system using stripline dipoles.

In an alternative example shown FIG. 10, a pair of fast kick magnets 1004 and 1008 were inserted downstream of the last primary bend, two stripline dipoles or a stripline plus a normal conducting kHz magnet 1012, while preserving the 1 m SAD with kicks of +/−10 degrees and vertical out of plane scan of +/−0.125 meter.

The table below summarizes the field strengths of the scanning magnets for this example and using a stripline dipole technology because the 4-5 T requirements and fast field scanning cannot be achieved by superconducting magnets. In a further example the collimation section could be moved to the straight section after the first bend in the upward section.

| Magnet code name | Type | Rep rate | Length (cm) | Gap × Aperture (cm) | B field (T) | Bend (deg) |
| --- | --- | --- | --- | --- | --- | --- |
| Scan Magnet #1 | Stripline | KHz | 10 | 1 × 1 | 4.1 | 0-±9.74 |
| Scan Magnet #2 | NC | KHz | 30 | 1 × 26 | 1.38 | 0-±9.74 |

Figure 11:
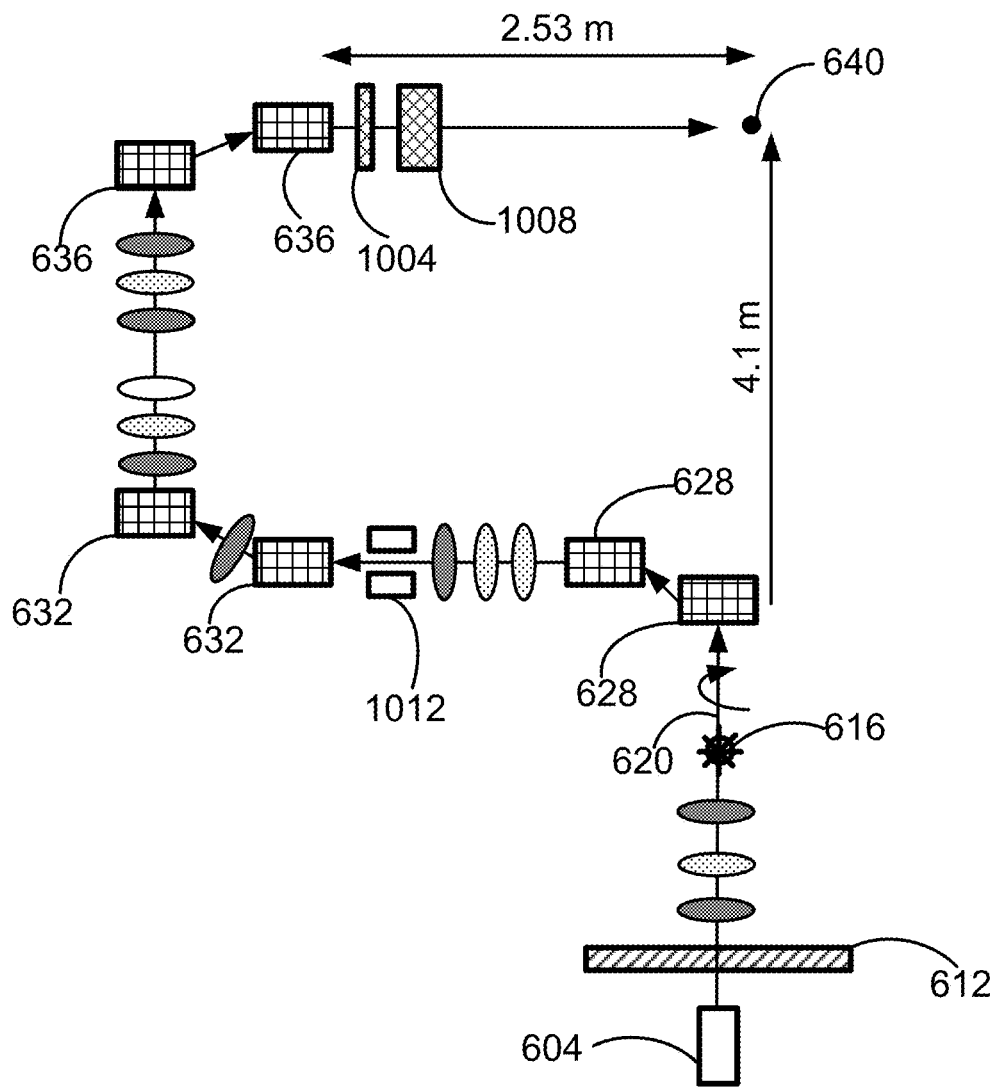
FIG. 11 is an example of a layout of a compact single collimator gantry using stripline dipoles for the primary bends.

FIG. 11 is an example of a layout of a compact single collimator gantry and upstream components using stripline dipoles for the primary bends. The obtained momentum collimation was $\Delta p/p$ of ±1/3 of a percent, well below the desired ±2% $\Delta p/p$. In a further example a quadrupole was embedded in the second pair of primary bends to cancel dispersion and its first derivative at isocenter.

In still another example the quadrupoles were limited to magnetic fields of 1 T at 1 cm (≤~100 T/m, k value of 41 m-2) to prepare for a larger aperture quadrupoles if needed. The compact nature of these stripline dipoles allows for greatly reduced quadrupole distances and correspondingly reduced beta functions and beam sizes. The table below is an example of the parameters used for operating the solenoid and stripline dipoles.

| Magnet code name | Type | Rep rate | Length (cm) | Gap × Aperture (cm) | B field (T) | Bend (deg) |
| --- | --- | --- | --- | --- | --- | --- |
| Solenoid | Stripline or SC | kHz or DC | 55 | 4.0 (diameter) | 14.2 | — |
| D1GAN-D6GAN (6 magnets) | Stripline | kHz | 40 | 1 × 5 | 4.7 | 45 |

The following table is an example of the corresponding quadrupole parameters.

| Magnet code name | Type | Rep rate | Length (cm) | Aperture diameter (cm) | Gradient (T/m) | Poletip field (T) |
| --- | --- | --- | --- | --- | --- | --- |
| Q1UP | NC | DC | 16 | 1.5 | 107 | 0.8 |
| Q2UP | NC | DC | 16 | 1.5 | 90 | 0.7 |
| Q3UP | NC | DC | 16 | 1.5 | 71 | 0.5 |
| Q4UP | NC | DC | 8 | 1.5 | 43 | 0.3 |
| Q1GAN | NC | DC | 8 | 1.5 | 76 | 0.2 |
| Q2GAN | NC | DC | 16 | 1.5 | 57 | 0.4 |
| Q3GAN | NC | DC | 8 | 1.5 | 65 | 0.5 |
| Q4GAN | NC | DC | 8 | 1.5 | 30 | 0.5 |
| Q5GAN | NC | DC | 8 | 1.5 | 28 | 0.2 |
| Q6GAN | NC | DC | 16 | 1.5 | 51 | 0.4 |
| Q7GAN | NC | DC | 8 | 1.5 | 42 | 0.3 |
| Q8GAN | NC | DC | 8 | 1.5 | 75 | 0.6 |
| Q9GAN | NC | DC | 16 | 1.5 | 63 | 0.5 |
| Q10GAN | NC | DC | 16 | 1.5 | 58 | 0.4 |

In another example Superferric superconducting dipoles can replace the stripline dipoles and retain essentially the same gantry optics and components. A sector dipole is more compatible with scanning and scanning coils could be installed in the interior of the last dipole. However, the sector edge focusing did not provide optics compatible with a small beam size at isocenter and the requirements for momentum collimation. Keeping the scanning system downstream of the last dipole bend does minimize the SC aperture. However, the first scanning magnet is high field and fast which is inconsistent with SC technology so this magnet has to be similar to the normal conducting downstream scanning magnet. In a further example the height of the gantry was 3 m. In an alternative example the gap in the downstream SC bend magnet is larger than previous examples to allow for embedded fast scanning coils. In a further example focusing coils can be incorporated in the bend dipoles for both SC and NC versions making them combined function magnetics and the optics more versatile.

In another example the compact high-field dipoles are replaced with normal conducting dipoles of 1.5 to 1.7 T. The lowered field changes the optics significantly due to both reduced edge and body focusing effects and greatly increased length. The length is 50% larger and the height is 4.5 m. The size of a gantry is almost completely dictated by the bend strengths. In a further example some length reduction can be achieved by moving the collimator to the upstream leg.

The table below is an example of solenoid magnet and dipole magnets and technical parameters for normal conducting structure evaluated at 250 MeV.

| Magnet code name | Type | Rep rate | Length (cm) | Gap × Aperture (cm) | B field (T) | Bend (deg) |
|---|---|---|---|---|---|---|
| Solenoid | Stripline or SC | kHz or DC | 55 | 4.0 (diameter) | 14.2 | — |
| D1GAN-D6GAN (6 magnets) | NC | kHz | 120 | 2 × 14-15 | 1.6 | 45 |
| Scan Magnet #1 | Stripline | KHz | 10 | 1 × 1 | 4.1 | 0-±9.74 |
| Scan Magnet #2 | NC | KHz | 30 | 1 × 26 | 1.38 | 0-±9.74 |

An example of a quadrupole magnets and technical parameters for normal conducting structure evaluated at 250 MeV.

| Magnet code name | Type | Rep rate | Length (cm) | Aperture diameter (cm) | Gradient (T/m) | Poletip field (T) |
|---|---|---|---|---|---|---|
| Q1GAN | NC | DC | 6 | 1.5 | 5 | 0.1 |
| Q2GAN | NC | DC | 6 | 1.5 | 27 | 0.4 |
| Q3GAN | NC | DC | 6 | 1.5 | 77 | 1.1 |
| Q4GAN | NC | DC | 6 | 1.5 | 77 | 1.1 |
| Q5GAN | NC | DC | 6 | 1.5 | 79 | 1.2 |
| Q6GAN | NC | DC | 12 | 1.5 | 76 | 1.1 |
| Q7GAN | NC | DC | 6 | 1.5 | 109 | 1.6 |
| Q8GAN | NC | DC | 6 | 1.5 | 46 | 0.7 |
| Q9GAN | NC | DC | 12 | 1.5 | 57 | 0.9 |
| Q10GAN | NC | DC | 6 | 1.5 | 93 | 1.4 |
| Q10GAN | NC | DC | 6 | 1.5 | 28 | 0.2 |

The performance of the examples above was verified by beam tracking. The starting distribution was characterized as an elliptical phase space and the outer beam ellipse tracked all the way through to isocenter. Only the outer ellipse needs to be tracked to determine the beam envelope at isocenter. The initial outer phase space ellipse could be described by ±50 microns and ±0.052 rad opening. The ellipses are symmetrical for the x coordinate and the y coordinate is the same.

In one example a system for delivering charged particles to treat a patient, comprising: an ion source configured to provide an ion beam substantially symmetric in phase space; a conduit for providing a path for the ion beam; at least one electromagnet associated with the conduit, the at least one electromagnet being configured to direct the ion beam; a rotatable gantry for supporting the at least one electromagnet and for rotating the at least one electromagnet about a patient treatment zone; and at least one processor configured to cause the at least one electromagnet to supply a substantially consistent electromagnetic field to phase space-symmetric ion beam independent of an angle of rotation of the at least one electromagnet on the rotatable gantry. In a further example the at least one electromagnet includes a plurality of electromagnets, and wherein the at least one processor is configured to cause each electromagnet to supply a differing consistent electromagnetic field. In a further example the ion source includes an electromagnetic radiation source configured to provide an electromagnetic radiation beam for irradiating an ion-generating target, to thereby produce the phase space-symmetric ion beam. In a further example the ion beam includes one or more of focusing, diverting, and scanning the ion beam. In a further example at least one electromagnet includes a quadrupole. In a further example at least one electromagnet includes a solenoid.

In one example a system for treating a target volume with ions, the system comprising: an ion source configured to provide an ion beam for use in scanning the target volume in a first direction and in a second direction; a movable platform for supporting a patient; a motor for moving the platform relative to the ion beam; and at least one processor configured to cause rastering of the target volume by: scanning the ion beam across the target volume in a first direction; and controlling the motor to move a patient on the movable platform in a second direction. In a further example the at least one processor is configured to cause rastering of the target volume by changing an energy of the ion beam so as to vary an interaction depth of the ion beam along a third depth axis orthogonal to a plane defined by the first fast axis and the second slow axis. In a further example scanning the ion beam across the target volume in the first direction includes directing the ion beam with at least one electromagnet. In a further example the ion source includes an electromagnetic radiation source for irradiating an ion-generating target with an electromagnetic radiation beam to thereby generate the ion beam. In a further example the first direction is a fast direction and the second direction is a slow direction.

To verify the performance of the beam delivery system it is also important to track stability off momentum. The solenoid channel provides better momentum stability because it provides stronger focusing. However a quadrupole channel can support correction systems for chromatic aberrations.

Outer beam coordinates have been tracked for the solenoid (left) capture channel and outer beam coordinates tracked for the quadrupole capture channel. For 1% Δp/p in the solenoidal channel and 0.5% in the quadrupole channel, the spot size at isocenter increases by about a factor of 3. Chromatic correction nominally increases the off-momentum acceptance by a factor of 2.

In summary examples of delivery systems can include:
a capture system comprising a 10-15 T solenoid or a SC or NC quadrupole capture system which converts the angular divergence of the beam source by a factor of 5; pairs of 5 T bend magnets implemented as stripline or SC magnets; momentum collimation optics comprised of triplet sets of quadrupoles; a primary momentum collimator installed in first leg of gantry. Further examples include rotationally invariant optics at coupling point with gantry.

Further examples of scanning systems include; fast magnets downstream of last primary bend, and a fast strong first scanning magnet.

In a further example, rapid energy change on millisecond timescales can be achieved by ramping the conventional magnetic components of the gantry. In a further example the magnets comprise of laminated magnets.

What is claimed is:

1. A system for delivering charged particles to treat a patient, comprising:
    a laser-driven ion source with an ion-generating target with a patterned surface, the ion source including a laser radiation source configured to provide a laser radiation beam for irradiating the ion-generating target the ion source
    configured to provide an ion beam substantially symmetric in phase space;
    a conduit for providing a path for the ion beam;
    at least one electromagnet associated with the conduit, the at least one electromagnet being configured to direct the ion beam substantially symmetric in phase space; and
    a rotatable gantry for supporting the at least one electromagnet and for rotating the at least one electromagnet about a patient treatment zone;
    wherein the substantially symmetric ion beam is circular with the same divergence in all directions so that rotation of the gantry does not impact the
    ion beam at isocenter of the gantry.

2. The system according to claim 1 wherein the at least one electromagnet includes a plurality of electromagnets, and wherein at least one processor is configured to cause each electromagnet to supply a differing consistent electromagnetic field.

3. The system according to claim 1 wherein directing the ion beam includes one or more of focusing, diverting, and scanning the ion beam.

4. The system according to claim 1 wherein the at least one electromagnet includes a quadrupole.

5. The system according to claim 1 wherein the at least one electromagnet includes a solenoid located at a distance from the gantry and providing a magnetic field configured to focus equally in all directions.

6. The system according to claim 1 wherein the ion-generating target is at least one target made on a substrate consisting of one of sapphire, silicon, carbon or plastics material.

7. The system according to claim 1 wherein the patterned surface of the target is irradiated by an electromagnetic radiation source and wherein the patterned surface is a layer of filaments having substantially uniform direction or nano-crescent shaped structures scattered on a surface of a substrate of the target all aligned in the same direction.

8. The system according to claim 1 wherein the patterned surface of the target is configured to produce a substantially symmetric in phase space symmetric ion beam.

* * * * *